(12) United States Patent
Stritzke et al.

(10) Patent No.: US 7,825,125 B2
(45) Date of Patent: *Nov. 2, 2010

(54) AMORPHOUS ARIPIPRAZOLE AND PROCESS FOR THE PREPARATION THEREOF

(75) Inventors: Katja Stritzke, Hamburg (DE); Uwe Löffler, Tornesch (DE); Klaus Glänzer, Hamburg (DE)

(73) Assignee: Helm AG, Hamburg (DE)

( * ) Notice: Subject to any disclaimer, the term of this patent is extended or adjusted under 35 U.S.C. 154(b) by 1067 days.

This patent is subject to a terminal disclaimer.

(21) Appl. No.: 11/463,062

(22) Filed: Aug. 8, 2006

(65) Prior Publication Data

US 2008/0020038 A1    Jan. 24, 2008

(30) Foreign Application Priority Data

Jul. 20, 2006  (EP)  .................... 06117595

(51) Int. Cl.
    *A61K 31/497* (2006.01)
    *C07D 401/12* (2006.01)
(52) U.S. Cl. ................. 514/253.07; 544/363
(58) Field of Classification Search ............ 514/253.07; 544/363
    See application file for complete search history.

(56) References Cited

U.S. PATENT DOCUMENTS

| 4,734,416 A | 3/1988 | Banno et al. |
| 5,006,528 A | 4/1991 | Oshiro et al. |
| 2004/0170672 A1 | 9/2004 | Selzer |
| 2004/0247870 A1 | 12/2004 | Brown et al. |
| 2005/0245539 A1 | 11/2005 | Mendla et al. |
| 2005/0272742 A1 | 12/2005 | Worthen et al. |
| 2008/0020038 A1 | 1/2008 | Stritzke et al. |
| 2008/0280921 A1* | 11/2008 | Dreyer et al. .......... 514/253.07 |

FOREIGN PATENT DOCUMENTS

| EP | 1398040 | 3/2004 |
| EP | 1 419 776 | 5/2004 |
| EP | 1 330 249 | 4/2006 |
| WO | WO 03/026659 | 4/2003 |
| WO | WO 2004/083183 | 9/2004 |
| WO | WO 2004/106322 | 12/2004 |
| WO | WO 2005/009990 | 2/2005 |
| WO | WO 2005/016262 | 2/2005 |
| WO | WO 2005/058835 | 6/2005 |
| WO | WO 2006/053781 | 5/2006 |
| WO | WO 2006/079549 | 8/2006 |
| WO | WO 2007/073389 | 6/2007 |
| WO | WO 2008/020820 | 2/2008 |

OTHER PUBLICATIONS

Aoki et al., "Study on Crystal Transformation of ARIPIPRAZOL," The Proceedings of the 4$^{th}$ Japanese-Korea Symposium on Separation Technology, CR.119 (Oct. 6-8, 1990 pp. 937-940.
www.fda.gov/cder/foi/nda/2002/21-436, Abilify_biophamr_P2.
FDA, Enforcement Report, Aug. 25, 2004 and Jul. 6, 2005.
Office Action issued Jan. 25, 2010 in U.S. Appl. No. 12/131,618.

* cited by examiner

*Primary Examiner*—James O Wilson
*Assistant Examiner*—Ebenezer Sackey
(74) *Attorney, Agent, or Firm*—Swanson & Bratschun, L.L.C.

(57) ABSTRACT

Morphologically stabilized amorphous aripiprazole and process for preparing the same.

41 Claims, 4 Drawing Sheets

AMORPHOUS ARIPIPRAZOLE AND PROCESS FOR THE PREPARATION THEREOF

RELATED APPLICATION

This application claims priority to European Application Serial No. 06117595.6, filed Jul. 20, 2006, entitled "Amorphous Aripiprazole and Process for the Preparation thereof", which is incorporated herein by reference in its entirety.

FIELD OF INVENTION

The present invention relates to oral formulations containing morphologically stabilized amorphous aripiprazole which has enhanced dissolution abilities. Another aspect of the invention relates to pharmaceutical dosage forms containing stabilized amorphous aripiprazole which can be used for instance for the treatment of schizophrenia and psychotic disorders.

BACKGROUND OF THE INVENTION

Aripiprazole, 7-{4-[4-(2,3-dichlorophenyl)-1-piperazinyl]-butoxy}-3,4-dihydro carbostyril or 7-{4-[4-(2,3-dichlorophenyl)-1-piperazinyl]-butoxy}-3,4-dihydro-2(1H)-quinolinone, is an atypical antipsychotic agent useful for the treatment of schizophrenia. Schizophrenia is a common type of psychosis characterized by delusions, hallucinations and extensive withdrawal from others. The preparation of aripiprazole and other carbostyril derivatives is described in U.S. Pat. No. 4,734,416 and U.S. Pat. No. 5,006,528. These processes do not result in the formation of well defined, reproducible forms of aripiprazole.

Aripiprazole is known in several polymorphic forms. The Proceedings of the 4$^{th}$ Japanese-Korean Symposium on Separation Technology (Oct. 6-8, 1996) state that, aripiprazole anhydride crystals exist as anhydrous type-I crystals (conventional anhydride), anhydrous type-II crystals, and type III hydrate (conventional hydrate); the type-I crystals of aripiprazole anhydride (conventional anhydride) can be prepared by recrystallization from an ethanol solution of aripiprazole, or by heating aripiprazole hydrate at 80° C. The type-II crystals of aripiprazole anhydride can be prepared by heating conventional anhydride at 130° to 140° C. for 15 hours. Type III crystals (conventional hydrate) were recrystallized from alcoholic solvent containing up to 20% (v/v) of water.

The hygroscopicity of the conventional anhydride crystals makes them difficult to handle since costly and burdensome measures must be taken in order ensure they are not exposed to moisture during preparation and formulation. When exposed to moisture, the conventional anhydrous forms of aripiprazole absorb water and convert to hydrous forms such as the monohydrate. The hydrous forms of aripiprazole have the disadvantage of being less soluble than the anhydrous forms. Moreover, variation in the amount of hydrous versus anhydrous aripiprazole from batch to batch makes it difficult to meet the specifications set by drug regulatory authorities. Furthermore, the solubility of aripiprazole is pH-dependent which influence the dissolution rate.

Numerous attempts have been made to overcome these disadvantages.

To ensure appropriate dissolution of poorly soluble drugs the drugs are commonly used in particle sizes smaller 50 μm. The small particle sizes are usually obtained by energy involved processes like extensive milling, micronization or grinding.

EP 1 330 249 And EP 1 419 776 disclose polymorphic modifications of aripiprazole which are said to have reduced hygroscopicity, such as anhydride B. Anhydride B can be obtained by milling conventional hydrate to provide intermediary hydrate A (particle size less 50 μm), which is converted to aripiprazole form B by heating to 90-125° C. for 3 to 50 hours. Anhydride B can be converted to a glassy state by heating to about 170° C. and cooling to room temperature. The glassy form of aripiprazole anhydride forms aripiprazole anhydride crystals of form G upon storing. In addition to hydrate A and anhydrides B and G aripiprazole anhydride crystals of forms C to F are described.

EP 1 606 262 discloses two crystalline forms of aripiprazole and four crystalline forms of aripiprazole hydrochloride which are said to be stable over the time and to be reproducible.

WO 2005/009990 discloses crystalline forms of aripiprazole, aripiprazole methanolate and aripiprazole ethylene dichloride solvate. These crystalline forms of aripiprazole are said to be non hygroscopic and to have no tendency to convert to other forms.

WO 2004/106322 describes the preparation of polymorphic forms II, II and IV of aripiprazole. Form II is described as having a melting point of 133 to 135° C., Form III of 122 to 125° C. and Form IV of 146 to 149° C.

WO 2005/058835 discloses anhydrous aripiprazole crystalline forms I, II, VI, VIII, X, XI, XII, XIV, XIX, XX and methods for preparing the same. These forms of aripiprazole are said to be non-hygroscopic and to maintain compound stability during storage. They can be prepared directly by slurrying without heating a preexisting hydrate crystal form.

None of the above forms of aripiprazole is completely satisfactory. For instance, during approval of aripiprazole tablets in Europe and the United States the 20- and 30-mg tablets had to be redesigned because they exhibited less than complete and slower dissolution than other aripiprazole tablet strengths at pH 1.2 (see www.fda.gov/cder/foi/nda/2002/21-436_Abilify_biopharmr_P2). In spite of this effort, the manufacturer had to recall several batches of tablets due to dissolution failure (FDA, Enforcement Report 25.08.2004 and 06.07.2005).

As can be seen from the above, there is a strong need for aripiprazole having a stable morphology and showing defined and stable dissolution rates.

It is an object of the invention to provide aripiprazole in morphologically stable form with good solubility in aqueous systems which can be easily prepared.

SUMMARY OF THE INVENTION

The present invention relates to oral formulations containing morphologically stable amorphous aripiprazole which has enhanced dissolution abilities.

The invention provides aripiprazole or a pharmaceutically acceptable salt thereof in stabilized amorphous form. The preparation of the amorphous aripiprazole of the present invention does not require grinding, the use of water-free conditions or the use of special polymorphic forms as starting materials. The dissolution rate of the stabilized amorphous aripiprazole of the present invention is not influenced by the formation of hydrates during storage and does therefore not require protection against moisture during storage.

Another aspect of the invention relates to pharmaceutical compositions comprising morphologically stabilized amorphous aripiprazole which can be used e.g. for the treatment of schizophrenia and psychotic disorders.

A further aspect of the invention relates to a process for preparing morphologically stabilized amorphous aripiprazole.

The above objects are achieved by pharmaceutical compositions comprising amorphous aripiprazole or a pharmaceutically acceptable salt thereof and at least one stabilizing agent.

DETAILED DESCRIPTION OF THE INVENTION

The present invention for the first time provides amorphous aripiprazole or a pharmaceutically acceptable salt thereof which is morphologically stable as well as pharmaceutical composition comprising morphologically stable amorphous aripiprazole or a salt thereof. The pharmaceutical compositions of the present invention preferably contain at least one stabilizing agent, i.e. an agent which stabilizes aripiprazole in its amorphous form and prevents crystallization thereof. In the following, these mixtures of amorphous aripiprazole with at least one stabilizing agent will also be referred to as morphologically stabilized amorphous aripiprazole or stabilized amorphous aripiprazole.

The morphologically stabilized amorphous aripiprazole of the present invention may comprise minor amounts of crystalline aripiprazole. Preferably the amorphous aripiprazole of the invention comprises less than 20% by weight of crystalline aripiprazole, more preferably less than 10% by weight, even more preferably less than 5% by weight, e.g. less than 2% by weight, based on the total amount of aripiprazole. Most preferably the stabilized aripiprazole of the present invention comprises substantially no crystalline aripiprazole.

The stabilized aripiprazole of the present invention preferably comprises aripiprazole and stabilizing agent in a weight ratio of 1:20 to 5:1. According to one preferred embodiment of the present invention the compositions comprise 4.8 to 83.3 wt.-% of aripiprazole, based on the total weight of the composition. It is further preferred that the compositions comprise 3.8 to 66.7 wt.-% of amorphous aripiprazole, i.e. the amount of crystalline aripiprazole is within a range of 0 to 16.6 wt.-%, based on the total weight of the composition.

It was surprisingly found that the stabilized amorphous aripiprazole of the present invention is better soluble in aqueous systems than the known crystalline forms of aripiprazole. It can be stored for prolonged time periods without changing its morphological structure, i.e. without crystallization. It was particularly surprising to find that the storage stability is not impaired by the presence of minor amounts of crystalline aripiprazole which would have been expected to induce crystallization of the whole material. Even after storage the morphologically stabilized amorphous aripiprazole of the present invention shows no significant change in the dissolution abilities.

According to the present invention aripiprazole is stabilized in amorphous form by admixture with at least one stabilizing agent which is selected from the group consisting of embedding materials and/or solubilizers.

Preferred stabilizing agents are polyvinyl pyrrolidone, polymethylacrylate, polyvinyl acetate phthalate, alkyl cellulose, hydroxyl alkyl cellulose, polyethylene glycol, polyethylene castor oil, polyethylene glycol sorbitan fatty acid, polyethylene polypropylene glycol, polyethylene oxide, polyoxyethylene alkyl ether, polyoxyethylene stearate, and derivatives of these substances, and mixtures thereof.

More preferred stabilizing agents are selected from polyvinyl pyrrolidone, polymethylacrylate, polyethylene glycol, polyethylene castor oil, polyoxyethylene hydrogenated castor oil, polyethylene glycol sorbitan fatty acid, polyoxyethylene stearate, and mixtures thereof.

The most preferred stabilizing agents are selected from polyethylene glycol having an average molecular weight within the range of 190 to 10,000, polyethylene oxide sorbitan mono-oleate, polyoxyl 40 hydrogenated castor oil, polyoxyl 35 castor oil, polyethylene glycol-15-hydroxystearate, dimethyl aminoethyl methacrylate, and vinyl pyrrolidone-vinyl acetate copolymer.

The stabilised amorphous aripiprazole of the present invention may comprise one or more stabilising agents. The use of 1 to 5 and in particular 2 to 3 stabilising agents is preferred.

If only one stabilizing agent is used, the stabilizing agent is preferably selected from polyethylene glycol sorbitan fatty acid, polyoxyethylene hydrogenated castor oil, polyoxyethylene castor oil, polyethylene glycol stearate, polymethacrylate, and derivatives thereof. More preferably the stabilizing agent is selected from polyethylene oxide sorbitan mono-oleate, polyoxyl 40 hydrogenated castor oil, polyoxyl 35 castor oil, polyethylene glycol-15-hydroxystearate, dimethyl aminoethyl methacrylate.

Compositions comprising at least two different stabilizing agents are preferred. If two different stabilizing agents are used the stabilizing agents are preferably selected from embedding materials and/or solubilizers. More preferably at least one stabilizing agent is selected from the group of embedding materials and at least one stabilizing agent is selected from the group of solubilizers.

According to the invention embedding materials are understood to be a kind of matrix or carrier material. Preferable embedding materials are physiologically acceptable polymers or copolymers based on vinyl compounds. The polyvinyl compounds may optionally be functionalized. They are preferably substituted by pyrrolidone, alkyl, ether, phenyl, amino, alkyl amino, dialkyl amino, ammonium, carboxy acid ester, carboxy acid, carboxy acid amide and/or acetate groups. Additionally, embedding materials can be selected from alkyl cellulose or hydroxyl alkyl cellulose.

According to the invention solubilizers are understood to be surfactants, or solubilizing, solubility enhancing agents or cosolvents for aripiprazole or a salt thereof. Preferred solubilizers are physiologically acceptable polymers or copolymers of ethylene glycol. The polyethylene compounds may optionally be functionalized. They are preferably substituted by substituents selected from fatty acids, fatty acid esters, fatty acid amides, castor oils, ethers, higher alcohols, alkyl, phenyl, amino, alkyl amino, dialkyl amino, or polyalcohol groups.

The first stabilizing agent is preferably selected from the group of embedding materials consisting of polyvinyl pyrrolidone, polymethylacrylates, polyvinyl acetate phthalate, alkyl cellulose, hydroxyl alkyl cellulose, derivatives of these substances, and mixtures thereof.

More preferably the first stabilizing agent is selected from polyvinyl pyrrolidone, vinylpyrrolidone-vinylacetate copolymer, methacrylic acid copolymer, amino alkyl methacrylate copolymer, methacrylic acid ester copolymer, ammonium alkyl methacrylate copolymer, methyl cellulose, ethyl cellulose, hydroxypropylmethyl cellulose, and mixtures thereof.

Most preferably the first stabilizing agent is selected from vinyl pyrrolidone-vinyl acetate copolymer, dimethyl aminoethyl methacrylate, and mixtures thereof.

The second stabilizing agent is preferably selected from solubilizers. Preferably the stabilizing agents are selected from compounds which cause a lowering of the melting point of an embedding compound and additionally have the property of a solubilizer. Preferably the second stabilizing agent is selected from of polyethylene glycol, polyethylene castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

More preferably the second stabilizing agent is selected from polyethylene glycol, polyethylene castor oil, polyoxyethylene hydrogenated castor oil, polyoxyethylene hydroxy stearate, polyethylene glycol sorbitan mono fatty acid, derivatives of these substances, and mixtures thereof.

Most preferably the second stabilizing agent is selected from polyethylene glycol having an average molecular weight within the range of 190 to 10,000, polyoxyl 35 castor oil, polyoxyl 40 hydrogenated castor oil, polyethylene glycol-15-hydroxystearate, polyoxyethylene sorbitan monooleate, and mixtures thereof.

The stabilized amorphous aripiprazole of the present invention preferably comprises 15 to 95 wt.-%, more preferably 25 to 93 wt.-% and most preferably 45 to 91 wt.-% of one ore more stabilizing agents, based on the total weight of aripiprazole and stabilizing agent(s).

In addition to the aripiprazole or a salt thereof and the one or more stabilizing agents the compositions of the invention comprises one ore more pharmaceutically acceptable excipients.

The pharmaceutical compositions of the present invention have preferably the form of oral dosage forms, such as granules, pellets, capsules, and in particular tablets, such as flash-melt tablets, oral dispersible tablets, sustained release tablets and immediate release tablets.

The pharmaceutical compositions of the present invention preferably comprise:

1 to 99.5 wt.-%, more preferably 5 to 75 wt.-% and most preferably 20 to 65 wt.-% of stabilized amorphous aripiprazole, and 0.05 to 99 wt.-%, more preferably 25 to 95 wt.-% and most preferably 35 to 80 wt.-% of further excipients.

The compositions preferably contain 1 to 200 mg, more preferably 1 to 100 mg and most preferably 1 to 30 mg of aripiprazole per unit dose.

The known pharmaceutical excipients can be used to prepare the pharmaceutical formulations of the invention, such as fillers, lubricants, disintegration aids, wetting agents, agents to improve the flow behavior, antioxidants, flavors, taste masking agents, pigments, dyes, lubricants and other additives, e.g. as disclosed in "Die Tablette", W. A. Ritschel and A. Bauer-Brandl, $2^{nd}$ ed., ECV-Edition Cantor publishers, 2002, the disclosure of which is incorporated herein by reference.

Preferred fillers are celluloses and cellulose derivatives, such as microcrystalline cellulose, native cellulose, hydroxypropyl cellulose, hydroxypropyl methyl cellulose, methyl cellulose, sugars, such as lactose, fructose, saccharose, glucose, maltose, sugar alcohols, such as lactitol, mannitol, sorbitol, xylitol, inorganic fillers, such as calcium phosphates and calcium sulfates, and starches, such as corn starch, potato starch, wheat starch, dextrins, and pregelatinized starches.

Preferred flavors are vanilla, cherry, lemon, and cacao. Preferred taste masking agents are ascorbic acid, citric acid, tartaric acid, apple acid and polymethylacrylate.

Preferred lubricants are fatty acids, such as stearic acid, fumaric acid, and salts thereof.

The tablets can be coated or uncoated. Sugar-coated tablets, gelatin-coated tablets, enteric coated tablets and film coated tablets are preferred as coated tablets. Furthermore, the tablets can be double tablets or multilayered tablets.

The pharmaceutical compositions of the present invention preferably have the form of immediate release tablets or orodispersible tablets.

Immediate release tablet preferably comprise:

1 to 99 wt.-%, preferably 35 to 70 wt.-% and more preferably 40 to 60 wt.-% of morphologically stabilized amorphous aripiprazole, 0 to 50 wt.-%, preferably 5 to 25 wt.-% and more preferably 8 to 20 wt.-% disintegrantion aids 0 to 90% wt.-%, preferably 10 to 60 wt.-% and more preferably 25 to 40 wt.-% filler, and 0.1 to 10 wt.-%, preferably 0.3 to 5 wt.-% and more preferably 0.5 to 3 wt.-% lubricant.

Orodispersible tablets preferably comprise:

1 to 99 wt.-%, preferably 3 to 50 wt.-% and more preferably 5 to 30 wt.-% morphologically stabilized amorphous aripiprazole, 0 to 10 wt.-%, preferably 0.3 to 6 wt.-% and more preferably 0.5 to 2 wt.-% taste masking agent, 0 to 90 wt.-%, preferably 40 to 90 wt.-% and more preferably 70 to 85 wt.-% filler, 0 to 50 wt.-% disintegrantion aids, 0.1 to 5 wt.-%, preferably 0.2 to 5 wt.-% and more preferably 0.3 to 3 wt.-% lubricant, and 0 to 5 wt.-% flavor.

The morphologically stabilized amorphous aripiprazole of the present invention can be prepared by mixing aripiprazole with a stabilizing agent or a mixture of stabilizing agents. Preferably two different stabilizing agents are used, as described above.

Preferably the aripiprazole is dissolved in stabilizing agent(s) at elevated temperature, preferably at a temperature within the range of 30 to 190° C., and then the solution is optionally cooled. If only one stabilizing agent is used for preparing morphologically stabilized amorphous aripiprazole the stabilizing agent is preferably selected from polyethylene glycol sorbitan fatty acid, such as polyethylene oxide sorbitan mono-oleate; polyoxyethylene hydrogenated castor oil, such as polyoxyl 40 hydrogenated castor oil; polyoxyethylene castor oil, such as polyoxyl 35 castor oil; polyethylene glycol stearate, such as polyethylene glycol-15-hydroxystearate; polymethacrylate, such as dimethyl aminoethyl methacrylate. The most preferred stabilizing agent is polyoxyl 35 castor oil.

If only one stabilizing agent is used, the stabilizing agent and aripiprazole are preferably used in a weight ratio of 1:5 to 5:1, more preferred 1:1. The compounds are preferably mixed at a temperature within the range of 40 to 190° C., more preferably 50 to 90° C., most preferably 60° to 75° C.

According to a preferred embodiment of the invention, aripiprazole is dissolved in a mixture of at least two different stabilizing agents at elevated temperature and then the solution is optionally cooled. According to this embodiment of the invention the first stabilizing agents is preferably selected from polyvinyl pyrrolidone, polymethacrylate, polyvinyl acetate phthalate, alkyl cellulose, hydroxyalkyl cellulose, derivatives of these substances, and mixtures thereof.

Most preferably the first stabilizing agent is polyvinyl pyrrolidone, such as vinylpyrrolidone-vinyl acetate copolymer or polymethacrylates, such as dimethyl aminoethyl methacrylate.

The second stabilizing agent is preferably selected from polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

Most preferably the second stabilizing agent is selected from polyethylene glycol with an average molecular weight from 190 to 10000, polyoxyl 35 castor oil, polyoxyl 40 hydrogenated castor oil, polyethylene glycol-15-hydroxystearate, polyoxyethylene sorbitan monooleate.

Most preferably a mixture of vinylpyrrolidone-vinyl acetate copolymer and polyethylene glycol having a molecular weight of about 6000 is used.

The first stabilizing agent, the second stabilizing agent and aripiprazole are preferably used in a weight ratio of 10:10:1 to 0.5:0.5:1, more preferably 5:5:1 to 2:2:1. The active ingredient and the stabilizing agent(s) are preferably mixed at a temperature within the range of 40 to 190° C., more preferably 100 to 180° C., most preferably 140° to 180° C.

The first stabilizing agent and the second stabilizing agent are preferably used in a weight ratio of 1:1.

Aripiprazole is preferably used in an amount of 5 to 50 wt.-%, based on the total weight of aripiprazole and stabilizing agent(s).

According to a further preferred embodiment of the invention aripiprazole is first dissolved in an organic solvent at elevated temperature, followed by the addition of at least one stabilizing agent. Alternatively, the aripiprazole may be added to a solution of the stabilizing agent(s) in an organic solvent. The compounds are mixed until a solution is obtained and then the organic solvent is removed.

Preferred organic solvents are ethanol, ethyl acetate, methanol, isopropyl alcohol, isopropyl acetate, dichloro methane, toluene, chloroform, preferred ethanol, acetone and mixtures thereof.

If an organic solvent is used, it is preferred to use at least two different stabilizing agents, more preferably a first and a second stabilizing agent as defined above.

If organic solvent is used it is preferred to use a first stabilizing agent which is preferably selected from polyvinyl pyrrolidone, polymethylacrylate, polyvinyl acetate phthalate, alkyl cellulose, hydroxyl alkyl cellulose, derivatives of these substances, and mixtures thereof.

Most preferably the first stabilizing agent is vinylpyrrolidone-vinyl acetate copolymer or dimethyl aminoethyl methacrylate.

The second stabilizing agent is preferably selected from polyoxyethylene castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

Most preferably the second stabilizing agent is selected from polyoxyl 35 castor oil and polyoxyl 40 hydrogenated castor oil.

According to the present invention it is particularly preferred to use a combination of polyoxyl 40 hydrogenated castor oil and vinylpyrrolidone-vinyl acetate copolymer, or a combination of polyoxyl 35 castor oil and vinylpyrrolidone-vinyl acetate copolymer as stabilising agents.

The first stabilizing agent, the second stabilizing agent and aripiprazole are preferably used in a weight ratio of 10:10:1 to 0.5:0.5:1, more preferably 4.5:4.5:1. The active ingredient, the organic solvent and the stabilizing agent(s) are preferably mixed at a temperature within the range of 40 to 120° C., more preferably 50 to 90° C., most preferably 60° to 75° C.

The first stabilizing agent and the second stabilizing agent are preferably used in a weight ratio of 1:1.

Aripiprazole is preferably used in an amount of 5 to 50 wt.-%, based on the total weight of aripiprazole and stabilizing agent(s).

To prepare morphologically stabilized amorphous aripiprazole any known polymorphic form, salt or solvate of aripiprazole can be used, for example conventional anhydride, conventional hydrate, type III, form A, form B, form I, form II, form III, form IV, VI, VIII, X, XI, XII, XIV, XIX, XX. The preparation is not limited to anhydride polymorphic forms of aripiprazole.

Aripiprazole of any particle size may be used. No previous grinding is necessary. Preferred salts of aripiprazole are the acid-addition salts, in particular the salts of hydrochloric acid, sulfuric acid, phosphoric acid, hydrobromic acid, oxalic acid, maleic acid, fumaric acid, malic acid, tartaric acid, citric acid, and benzoic acid.

The morphologically stabilized amorphous aripiprazole obtained by any of the above procedures can be used directly for the preparation of pharmaceutical compositions or may be first subjected to grinding, sieving, or milling.

Oral pharmaceutical formulations can be produced for instance by direct compression, dry-granulation, wet-granulation, preferably by melt extrusion, melt granulation or pelletization.

EXAMPLES

For the preparation of morphologically stabilized amorphous aripiprazole the conventional anhydride of aripiprazole prepared according to Example 1 of EP 0 367 141 A2 was used.

All X-ray diffraction measurements were performed in the transmission mode using the following conditions:

Cu-K$\alpha_1$-radiation ($\lambda$=1.54056 Å), U=40 kV, I=30 mA.

Primary Monochromator (curved Ge(111)).

Position Sensitive Detector, sample movement $\Delta\omega$.

Slits: 1 mm, 8 mm diameter.

Angle region: 2$\theta$=3 to 35°, steps $\Delta 2\theta$=0.2° (0.02°), t=18 s/step

Example 1

Preparation of Stabilized Amorphous Aripiprazole by Mixing the Active Ingredient with a Single Stabilizing Agent (Cremophor RH40)

22.5 g of polyoxyethylene castor oil (Cremophor RH 40) were heated in a glass vessel to T≈60° C. At that temperature 2.5 g of aripiprazole (conventional anhydride) were added with stirring to obtain a homogeneous solution. Stirring was continued for an additional 10 min., then the mixture was allowed to cool to room temperature.

Example 2

Preparation of Stabilized Amorphous Aripiprazole by Mixing the Active Ingredient with a Single Stabilizing Agent (Solutol HS 15)

22.5 g of polyethylene glycol-15-hydroxystearate (Solutol HS 15) were melted in a glass vessel at T≈60° C. At that temperature 2.5 g aripiprazole (conventional anhydride) were added with stirring to obtain a homogeneous solution. Stirring was continued for additional 10 min., then the mixture was allowed to cool down to room temperature.

Example 3

Preparation of Stabilized Amorphous Aripiprazole by Mixing the Active Ingredient with a Single Stabilizing Agent (Cremphor EL)

22.5 g of polyoxyethylene castor oil (Cremophor EL) were heated in a glass vessel to T≈60° C. At that temperature 2.5 g aripiprazole were added with stirring to obtain a homogeneous solution. Stirring was continued for additional 10 min., then the mixture was allowed to cool down to room temperature.

Example 4

Figure 1:
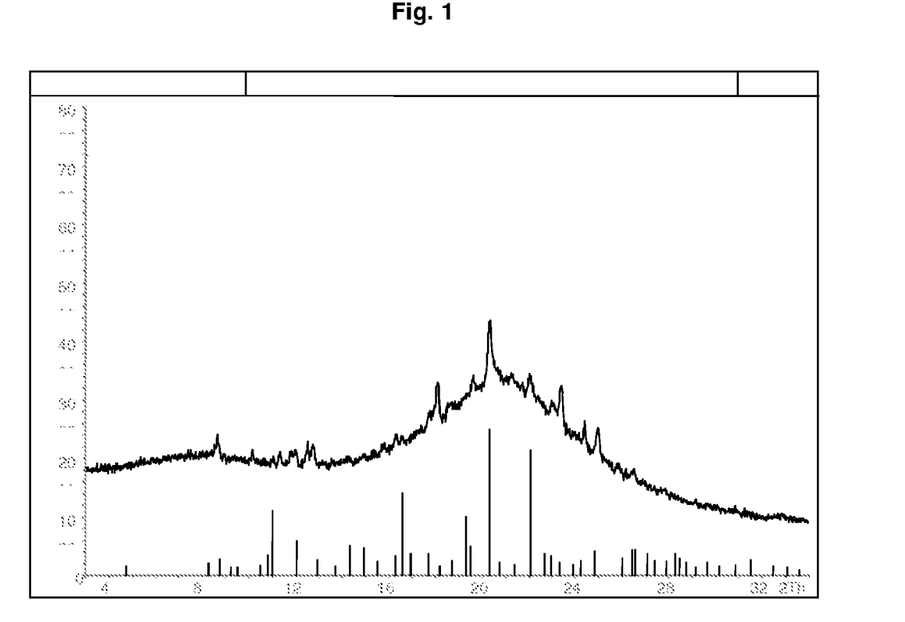
FIG. 1. shows the powder X-ray diffraction pattern of aripiprazole stabilized with polyoxyethylene hydrogenated castor oil (Cremophor RH 40) and polyvinyl pyrrolidone (Kollidon VA 64) according to Example 4.

Preparation of Stabilized Amorphous Aripiprazole by Mixing the Active Ingredient with Two Stabilizing Agents (Cremophor RH 40/Kollidon VA64) in the Presence of Organic Solvent 2.5 g of aripiprazole, 11.25 g of polyoxyethylene hydrogenated castor oil (Cremophor RH 40) and 11.25 g of polyvinyl pyrrolidone (Kollidon VA 64) were dissolved in 50 ml of absolute ethanol at T≈75° C.; a clear, yellowish solution was obtained. The solvent was removed at T≈45° C. with the aid of a rotary evaporator and the product was analyzed by X-ray diffraction measurement; the obtained spectrum is shown in FIG. 1.

Figure 6:
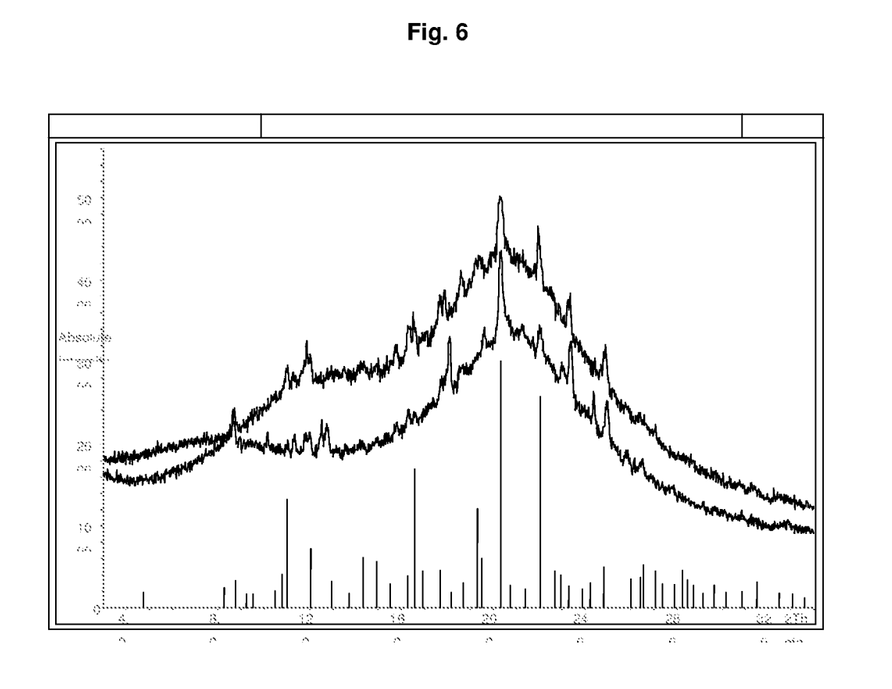
FIG. 6. shows the power X-ray diffraction pattern of aripiprazole stabilized with polyoxyethylene hydrogenated castor oil (Cremophor RH 40) and polyvinyl pyrrolidone (Kollidon VA 64) according to Example 4 after storage for 1 week at 50° C. and 80% humidity.

The X-ray diffraction pattern of the same product after one week of storage at 50° C. and 80% humidity is shown in FIG. 6 (lower curve). The upper curve shows the product before storage; no significant chance of the amorphous from of aripiprazole can be seen after storage.

Example 5

Figure 2:
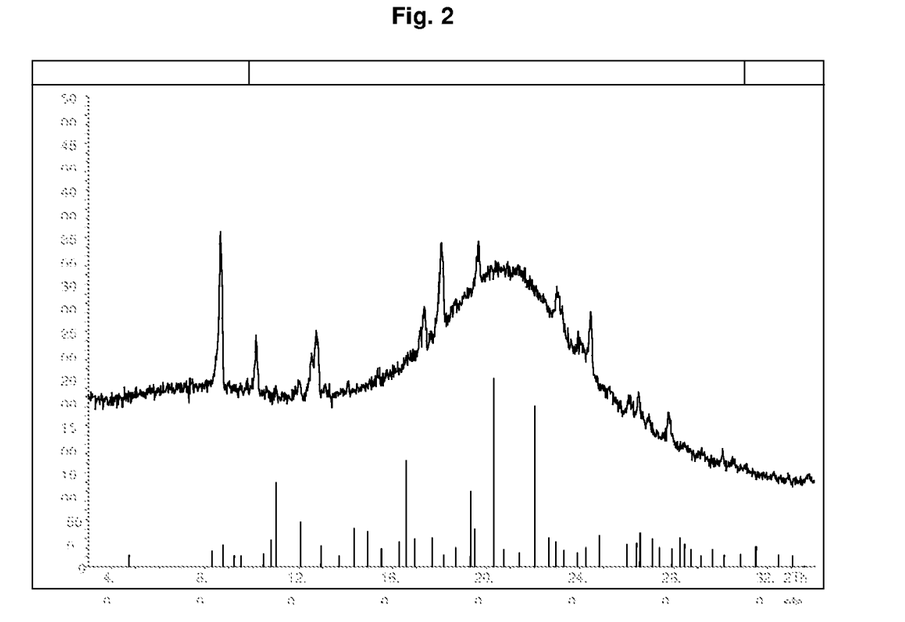
FIG. 2. shows the powder X-ray diffraction pattern of aripiprazole stabilized with polyoxyethylene hydrogenated castor oil (Cremophor EL) and polyvinyl pyrrolidone (Kollidon VA 64) according to Example 5.

Preparation of Stabilized Amorphous Aripiprazole by Mixing the Active Ingredient with a Two Stabilizing Agents (Cremophor EL/Kollidon) in the Presence of Organic Solvent The method of Example 4 was repeated but using 11.25 g of Cremophor EL instead of Cremophor RH 40. A clear, yellow solution was obtained. Removal of the solvent and X-ray diffraction measurement of the product gave the spectrum shown in FIG. 2.

Example 6

Preparation of Stabilized Amorphous Aripiprazole by Mixing the Active Ingredient with Two Stabilizing Agents (Macrogol 6000/Kollidon VA 64) in the Absence of Organic Solvent 10 g of polyethylene glycol (Macrogol 6000) and 10 g of polyvinyl pyrrolidone (Kollidon VA 64) were heated in a glass vessel to T≈150° C. to 180° C. At that temperature 4.98 g aripiprazole (Example 1) were added with stirring to obtain a homogeneous solution. Stirring was continued for an additional 10 min., the mixture was poured into a mortar and allowed to cool down to room temperature. X-ray diffraction measurement of the product resulted in the spectrum shown in FIG. 3.

Figure 3:
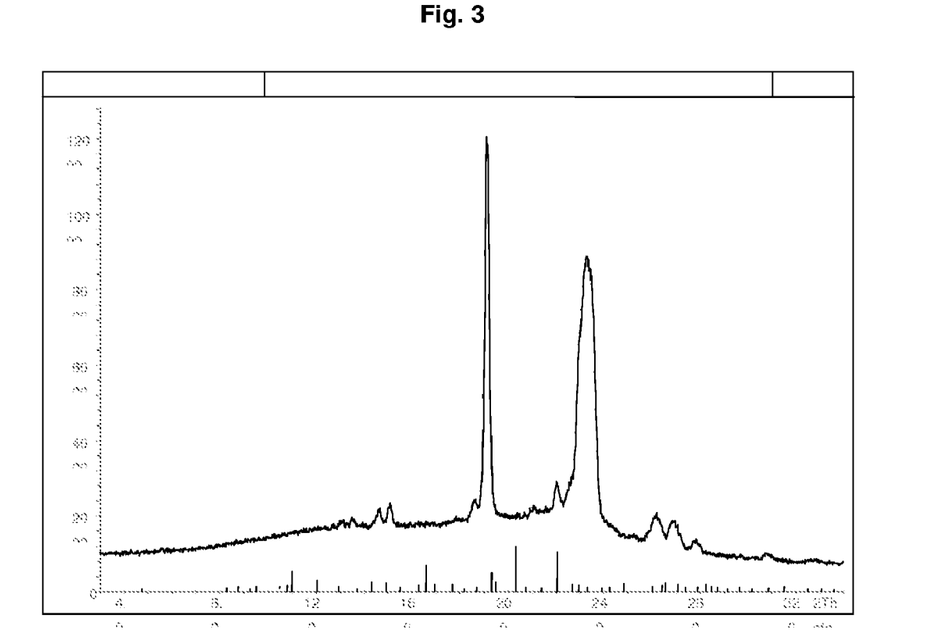
FIG. 3. shows the powder X-ray diffraction pattern of aripiprazole stabilized with polyethylene glycol (Macrogol 6000) and polyvinyl pyrrolidone (Kollidon VA 64) according to Example 6.
Figure 4:
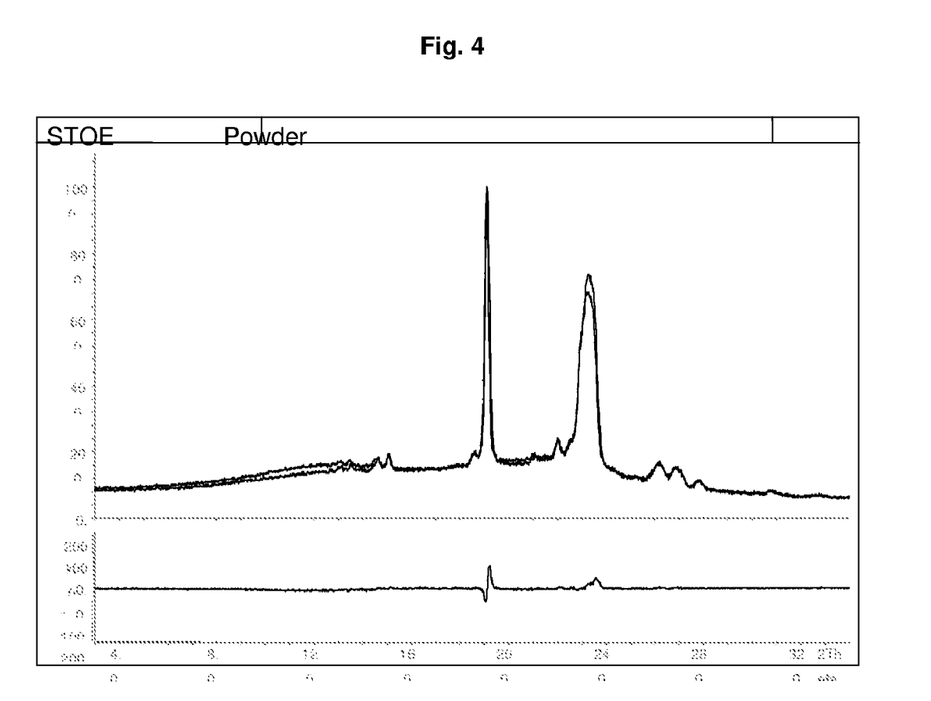
FIG. 4. shows the powder X-ray diffraction pattern of aripiprazole stabilized with polyethylene glycol (Macrogol 6000) and polyvinyl pyrrolidone (Kollidon VA 64) according to example 6, the powder X-ray diffraction pattern of a mixture of polyethylene glycol (Macrogol 6000) and polyvinyl pyrrolidone (Kollidon VA 64) without aripiprazole, and the difference spectrum of the first and second spectrum.

In the upper part of FIG. 4 the spectrum of FIG. 3 is overlaid with the spectrum of a mixture of Macrogol 6000 and Kollidon VA 64 without the active ingredient. In the lower part of FIG. 4 the difference of the two spectra is shown. It can be seen that the peaks of FIG. 3 must be caused by the stabilizing agents, i.e. the aripiprazole contained in the mixture is purely amorphous and does therefore not result in the formation of any additional peaks.

Example 7

Figure 5:
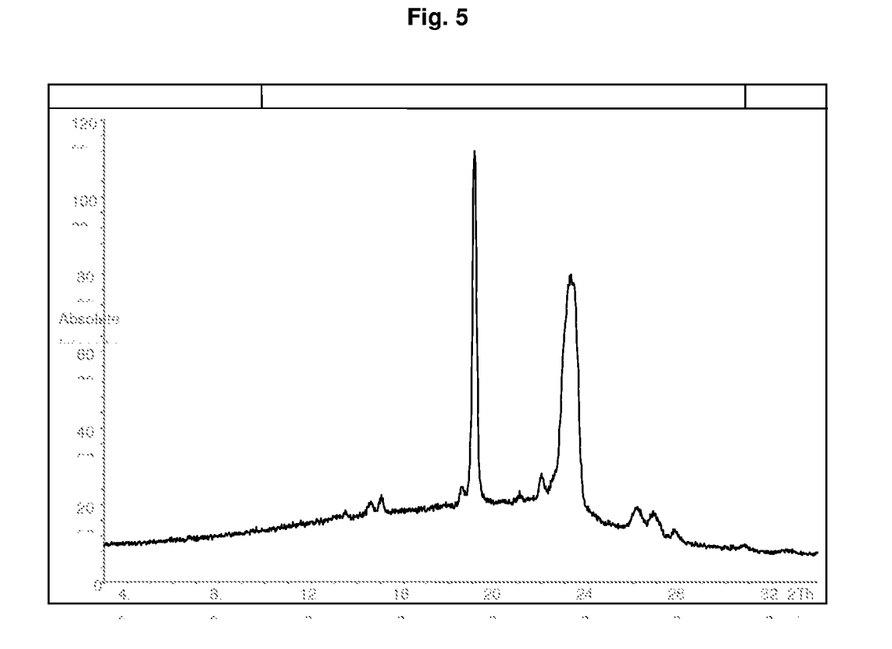
FIG. 5. shows the powder X-ray diffraction pattern of aripiprazole stabilized with polyethylene glycol (Macrogol 6000) and polyvinyl pyrrolidone (Kollidon VA 64) according to Example 7

Preparation of Stabilized Amorphous Aripiprazole by Mixing the Active Ingredient with Two Stabilizing Agents (Macrogol 6000/Kollidon VA 64) in the Absence of Organic Solvent 5.63 g of polyethylene glycol (Macrogol 6000) and 5.64 g of polyvinyl pyrrolidone (Kollidon VA 64) were heated in a glass vessel to T≈150° C. to 180° C. At that temperature 1.32 g aripiprazole were added with stirring to obtain a homogeneous solution. Stirring was continued for an additional 10 min., then the dispersion was poured into a mortar and allowed to cool down to room temperature. X-ray diffraction measurement of the product resulted in the spectrum shown in FIG. 5.

Example 8

Dissolution Rate of Stabilized Amorphous Aripiprazole

Figure 7:
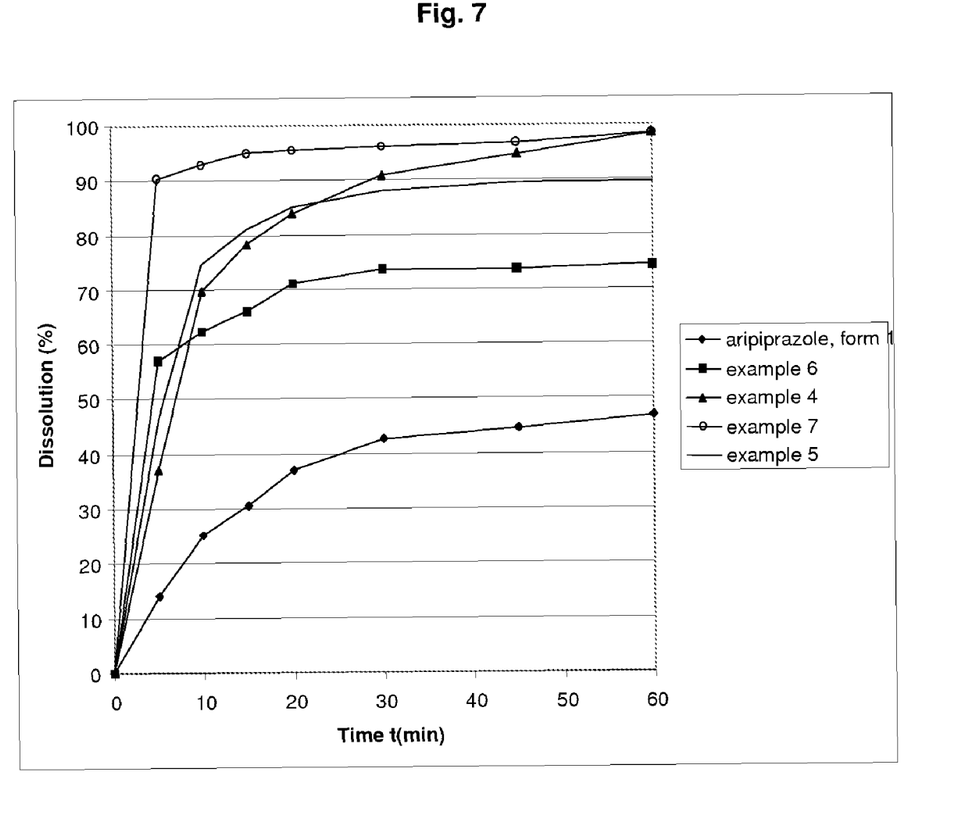
FIG. 7. shows the dissolution profile of crystalline aripiprazole form 1 in comparison with stabilized amorphous aripiprazole according to the present invention.

The dissolution rate of the morphologically stabilized amorphous aripiprazole of examples 4, 5, 6 and 7 was determined according to USP (900 ml HCL, 37° C., 60 rpm) using an amount of stabilized aripiprazole which corresponds to 10 mg of pure aripiprazole, and compared to the dissolution rate ground crystalline aripiprazole type 1 (10 mg) (EP 0 367 141 A2, Example 1). The dissolution profiles are shown in FIG. 7.

Example 9

Immediate Release Tablet Containing Stabilized Amorphous Aripiprazole

Immediate release tablets of the following composition were prepared by direct compression of mixture of the substances specified in Table 1 on tabletting machine (Frogerais OA).

TABLE I

Immediate release tablet

| Component | wt.-% | mg per tablet |
|---|---|---|
| stabilized amorphous aripiprazole (Ex 6)[1] | 52.6 | 50[2] |
| microcrystalline cellulose | 10.5 | 10 |
| Lactose monohydrate | 25.5 | 24.2 |
| Corn starch | 10.5 | 10 |
| Magnesium stearate | 0.8 | 0.8 |
| Total | 100 | 95 |

[1] Macrogol 6000:Kollidon V A64:Aripiprazole = 2:2:1
[2] = 10 mg aripiprazole

Example 10

Immediate Release Tablet Containing Stabilized Amorphous Aripiprazole

Immediate release tablets of the following composition were prepared by direct compression of mixture of the substances specified in Table 2 on tabletting machine (Frogerais OA).

TABLE 2

Immediate release tablet

| Component | wt-% | mg per tablet |
|---|---|---|
| stabilized amorphous aripiprazole (Ex. 6)[1] | 52.6 | 50[2] |
| Microcrystalline cellulose | 10.5 | 10 |
| Lactose monohydrate | 20.2 | 19.2 |
| Corn starch | 15.8 | 15 |
| Magnesium stearate | 0.8 | 0.8 |
| Total | 100 | 95 |

[1] Macrogol 6000:Kollidon V A64:Aripiprazole = 2:2:1
[2] = 10 mg aripiprazole

Example 11

Orodispersible Tablet Containing Stabilized Amorphous Aripiprazole

Orodispersible tablets of the following composition were prepared by direct compression of mixture of the substances specified in Table 3 on tabletting machine (Frogerais OA).

TABLE 3

Orodispersible tablet

| Component | wt.-% | mg per tablet |
|---|---|---|
| stabilized amorphous aripiprazole (Ex. 6)[1] | 13.9 | 50[2] |
| Ascorbic acid | 0.9 | 3.2 |
| Mannitol | 69.2 | 249.2 |
| Microcrystalline cellulose | 15.6 | 56.00 |
| Magnesium stearate | 0.4 | 1.6 |
| Aspartam | <1 | |
| Vanilla aroma | <1 | |
| Total | 100 | 360.00 |

[1] Macrogol 6000:Kollidon V A64:Aripiprazole = 2:2:1
[2] = 10 mg aripiprazole

The invention claimed is:

1. Morphologically stabilized amorphous aripiprazole or a pharmaceutically acceptable salt thereof.

2. A pharmaceutical composition comprising the morphologically stabilized amorphous aripiprazole or pharmaceutically acceptable salt thereof of claim 1, together with at least one pharmaceutically acceptable excipient.

3. The pharmaceutical composition of claim 2, comprising 1 to 99.5 wt.-% of morphologically stabilized amorphous aripiprazole, containing 0.1 to 95 wt.-% of stabilizing agent(s).

4. The pharmaceutical composition of claim 2, comprising:
   1 to 99.5 wt.-% morphologically stabilized amorphous aripiprazole, and
   0.5 to 99 wt.-% further excipients.

5. The morphologically stabilized amorphous aripiprazole or pharmaceutically acceptable salt thereof of claim 1, formulated as an oral pharmaceutical formulation selected from flash-melt tablets, oral dispersible tablets, sustained release tablets and immediate release tablets.

6. A composition comprising amorphous aripiprazole or a pharmaceutically acceptable salt thereof and at least one stabilizing agent.

7. The composition of claim 6 wherein the stabilizing agent is selected from the group consisting of polyvinyl pyrrolidone, polymethylacrylate, alkyl cellulose, hydroxylalkyl cellulose, polyvinyl acetate phthalate, polyethylene glycol, polyoxyethylene castor oil, polyoxyethylene hydrogenated castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

8. The composition of claim 7 wherein the stabilizing agent is selected from the group consisting of polyethylene glycol having an average molecular weight within the range of 190 to 10,000, polyethylene oxide sorbitan mono-oleate, polyoxyl 40 hydrogenated castor oil, polyoxyl 35 castor oil, polyethylene glycol-15-hydroxystearate, dimethyl aminoethyl methacrylate, and vinyl pyrrolidone-vinyl acetate copolymer.

9. The composition of claim 7, comprising at least two different stabilizing agents.

10. The composition of claim 9, comprising an embedding material as first stabilizing agent and a solubilizer as second stabilizing agent.

11. The composition of claim 9, comprising
a first stabilizing agent selected from the group consisting of polyvinyl pyrrolidone, polymethylacrylate, polyvinyl acetate phthalate, alkyl cellulose, hydroxyalkyl cellulose, derivatives of these substances, and mixtures thereof, and
a second stabilizing agent selected from the group consisting of polyethylene glycol, polyoxyethylene castor oil, polyoxyethylene hydrogenated castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

12. The composition of claim 11, wherein the first stabilizing agent is selected from the group consisting of vinyl pyrrolidone-vinyl acetate copolymer, dimethyl aminoethyl methacrylate, and mixtures thereof.

13. The composition of claim 11, wherein the second stabililzing agent is selected from the group consisting of polyethylene glycol having an average molecular weight within the range of 190 to 10,000, polyoxyl 35 castor oil, polyoxyl 40 hydrogenated castor oil, polyethylene glycol-15-hydroxystearate, polyoxyethylene sorbitan monooleate, and mixtures thereof.

14. The composition of any one of claim 9, comprising a first stabilizing agent and a second stabilizing agent in a weight ratio of 5:1 to 1:5.

15. The composition of claim 6, comprising 4.8 to 83.3 wt.-% of aripiprazole.

16. The composition of claim 6, comprising 3.8 to 66.7 wt.-% of amorphous aripiprazole.

17. A pharmaceutical composition comprising the morphologically stabilized amorphous aripiprazole or pharmaceutically acceptable salt thereof of claim 6, together with at least one pharmaceutically acceptable excipient.

18. A process for preparing morphologically stabilized amorphous aripiprazole comprising the mixing of aripiprazole with a stabilizing agent or mixture of stabilizing agents.

19. The process of claim 18, comprising the steps of
(a) dissolving aripiprazole in an organic solvent,
(b) adding at least one stabilizing agent, and
(c) removing the solvent.

20. The process of claim 19, wherein two different stabilizing agents are added in step (b).

21. The process of claim 20, comprising the addition of
a first stabilizing agent selected from the group consisting of polyvinyl pyrrolidone, polymethylacrylate, polyvinyl acetate phthalate, alkyl cellulose, hydroxyl alkyl cellulose, and derivatives and/or a mixture thereof, and
a second stabilizing agent selected from the group consisting of polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, and derivatives and/or a mixture thereof.

22. The process of claim 21, wherein the first stabilizing agent is selected from vinylpyrrolidone-vinyl acetate or dimethyl aminoethyl methacrylate.

23. The process of claim 21, wherein the second stabilizing agent is selected from the group consisting of polyethylene glycol with an average molecular weight from 190 to 10000, polyoxyl 35 castor oil, polyoxyl 40 hydrogenated castor oil, polyethylene glycol-15-hydroxystearate and polyoxyethylene sorbitan monooleate.

24. The process of claim 21, wherein the first stabilizing agent is vinylpyrrolidone-vinyl acetate copolymer and the second stabilizing agent is polyethylene glycol having a molecular weight of about 6000.

25. The process of claim 20, wherein the first stabilizing agent and the second stabilizing agent are used in a weight ratio of 1:5 to 5:1.

26. The process of claim 20, wherein the first stabilizing agent and the second stabilizing agent are used in a weight ratio of 1:1.

27. The process of claim 20, wherein the aripiprazole and stabilizing agent(s) are used in a weight ratio of 1:20 to 5:1.

28. The process of claim 20, wherein aripiprazole, first and second stabilizing agent are used in a weight ratio of 1:10:10 to 1:4.5:4.5.

29. The process of any one of claim 20, wherein the mixture of step (a) and/or (b) is heated at a temperature of 40 to 120° C.

30. The process of claim 20, wherein the organic solvent is selected from the group consisting of ethanol, ethyl acetate, methanol, isopropyl alcohol, isopropyl acetate, dichloro methane, toluene, chloroform, preferred ethanol, acetone and mixtures thereof.

31. The process of claim 18, comprising the steps of
(a) dissolving at least one stabilizing agent in an organic solvent,
(b) adding aripiprazole, and
(c) removing the solvent.

32. The process of claim 18, wherein the aripiprazole is dissolved in a mixture of at least two different stabilizing agents.

33. The process of claim 32, wherein the aripiprazole is dissolved in a mixture comprising
a first stabilizing agent selected from the group consisting of polyvinyl pyrrolidone, polymethylacrylate, polyvinyl acetate phthalate, alkyl cellulose, hydroxyl alkyl cellulose, or a mixture thereof, and
a second stabilizing agent selected from the group consisting of polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, and derivatives and/or a mixture thereof.

34. The process of claim 33, wherein the first stabilizing agent is selected from vinylpyrrolidone-vinyl acetate or dimethyl aminoethyl methacrylate.

35. The process of claim 33, wherein the second stabilizing agent is selected from the group consisting of polyoxyl 35 castor oil and polyoxyl 40 hydrogenated castor oil.

36. The process of claim 33, wherein the first and second stabilizing agents are selected from a combination of polyoxyl 40 hydrogenated castor oil and vinylpyrrolidone-vinyl acetate copolymer, or a combination of polyoxyl 35 castor oil and vinylpyrrolidone-vinyl acetate copolymer.

37. The process of claim 32, wherein the aripiprazole and stabilizing agent(s) are used in a weight ratio of 1:20 to 5:1.

38. The process of claim 32, wherein aripiprazole, first and second stabilizing agent are used in a weight ratio of 1:10:10 to 1:0.5:0.5.

39. The process of claim 32, wherein the mixture is heated at a temperature of 40 to 190° C.

40. A method for converting crystalline aripiprazole to morphologically stabilized amorphous aripiprazole said method comprising combining crystalline aripiprazole with at least two different stabilizing agents.

41. The method of claim 40, said method comprising combining crystalline aripiprazole with at least a first stabilizing agent selected from the group consisting of polyvinyl pyrrolidone, polymethylacrylate, polyvinyl acetate phthalate, alkyl cellulose, hydroxyl alkyl cellulose, or a mixture thereof, and a second stabilizing agent selected from the group consisting of polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, and derivatives and/or a mixture thereof.

* * * * *